United States Patent [19]

Marin Moga

[11] 3,957,866

[45] May 18, 1976

[54] CYCLOPENTYL CARBAMIDE DERIVATIVE AND PROCESS FOR ITS PRODUCTION

[75] Inventor: Antonio Camelo Marin Moga, Barcelona, Spain

[73] Assignee: J. Uriach & Cia S.A., Barcelona, Spain

[22] Filed: May 2, 1974

[21] Appl. No.: 466,412

Related U.S. Application Data

[63] Continuation-in-part of Ser. No. 182,187, Sept. 20, 1971, abandoned.

[30] Foreign Application Priority Data

Sept. 23, 1970 Spain .................................. 384463

[52] U.S. Cl. ......................... 260/553 DA; 424/322
[51] Int. Cl.² ..................................... C07C 127/16
[58] Field of Search ............................. 260/553 DA

[56] References Cited
UNITED STATES PATENTS

| | | | |
|---|---|---|---|
| 3,426,067 | 2/1969 | Weber et al. ............... | 260/553 DA |
| 3,448,149 | 6/1969 | Aumuller et al. ............ | 260/553 DA |

FOREIGN PATENTS OR APPLICATIONS

| | | | |
|---|---|---|---|
| 1,571,292 | 5/1969 | France ........................ | 260/553 DA |
| 746,505 | 8/1970 | Belgium ...................... | 260/553 DA |

*Primary Examiner*—Gerald A. Schwartz
*Attorney, Agent, or Firm*—Steinberg and Blake

[57] ABSTRACT

The invention relates to the new compound N-[4-beta-(0-anisamide-ethyl)-benzenesulphonyl]-N'-cyclopentylcarbamide and pharmaceutically acceptable salts thereof. The invention further relates to the production of this compound and its salts and the use of the compound and its salts to effect the lowering of blood sugar levels, that is for its glucoreduction activity.

2 Claims, No Drawings

CYCLOPENTYL CARBAMIDE DERIVATIVE AND PROCESS FOR ITS PRODUCTION

CROSS REFERENCE TO RELATED APPLICATION

This application is a continuation-in-part of my co-pending application Ser. No. 182,187, filed Sept. 20, 1971, for "Cyclopentyl Carbamide Derivatives and Process for its Production", now abandoned.

BACKGROUND OF THE INVENTION

Hypoglycemic agents that can be used orally for reduction of blood sugar levels, such as tolbutamide [1-butyl-3-(p-tolylsulfonyl) urea] have been used for many years. However the known agents suffer from numerous disadvantages and new agents having this effect have been sought.

SUMMARY OF THE INVENTION

Generally speaking, the present invention relates to N-[4-beta-(o-anisamide-ethyl)-benzenesulphonyl]-N'-cyclopentylcarbamide and its pharmaceutically acceptable salts such as the sodium salt, the potassium salt, etc., to pharmaceutical compositions containing the same, and to the use of this compound and its salts to effect the lowering of blood sugar levels.

The compound of the present invention has the following structural formula:

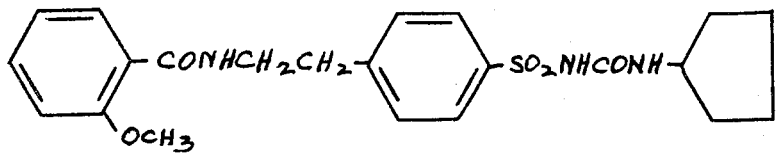

It is accordingly a primary object of the present invention to provide the new compound N-[4-beta-(o-anisamide-ethyl)-benzenesulphonyl]-N'-cyclopentyl-carbamide and physiologically compatible or pharmaceutically acceptable salts thereof.

It is another object of the present invention to provide pharmaceutical compositions thereof with any pharmaceutically acceptable carrier, particularly a carrier for oral administration.

It is yet a further object of the present invention to provide for the administration of the above compound and its salts to effect the lowering of blood sugar levels.

The present invention further provides for the method of producing the above compound.

The compounds of the present invention may, for example, be prepared by reacting 4-(beta-(o-anisamide)-ethyl)-benzenesulphonamide of the formula:

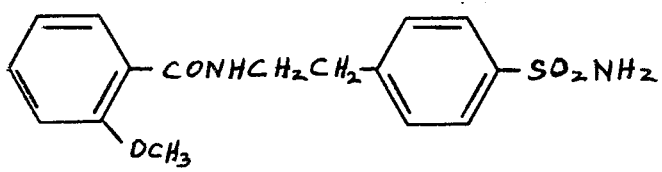

with ethyl chloroformate in a medium inert to the reaction. The reaction proceeds quite simply and the reaction conditions may be varied considerably.

The compound of the present invention, N-[4-beta-(o-anisamide-ethyl)-benzenesulphonyl]-N'-cyclopentylcarbamide may also be designated as N-[4-(beta-(2-methoxybenzamido)-ethyl)-benzenesulphonyl]-N'-cyclopentylurea.

This compound of the invention has the effect of providing an effective glucoreduction activity, that is the lowering of the blood sugar levels, by stimulating the release of insulin. However, unlike other closely related sulphonylureas, such as N-[4-(beta-(2-methoxybenzamido)-ethyl)-benzenesulphonyl]-N'-cyclohexylurea and N-[4-(beta-(2-methoxy-5-chlorobenzamido)-ethyl-benzene-sulphonyl]ethyl)-benzenesulphonyl]-N'-cyclopentylurea, provides the maximum insulin output at least twice as fast after administration. Thus, the compound of the present invention gives rise to a sharp increase in insulin output followed by slow diminution thereof. This difference in manner of acting results in much greater possibilities of use of the compound of the present invention to effect the lowering of blood sugar levels than with the other sulphonylureas mentioned above. Thus, whereas the other sulphonylureas have the effect of exhausting and abusing the pancreas so that the pancreas cannot recover between two consecutive doses thereof, the compound of the present invention acts in a much more effective manner which permits the use thereof clinically, which is not the case with the other mentioned compounds.

In addition, the compound of the present invention has much less of an inhibitory action on the pancreatic phosphodiesterase so that the use thereof provides much less of a probability of myocardial infarction incidence than in the case of the use of the other mentioned sulphonylureas.

DESCRIPTION OF PREFERRED EMBODIMENTS

The following examples are given to further illustrate the present invention. The scope of the invention is not, however, meant to be limited to the specific details of the examples.

EXAMPLE 1

This example describes a production of N-[4-beta-(o-anisamide-ethyl)benzenesulphonyl]-N'-cyclopentylcarbamide.

46.5 g of 4-(beta-(o-anisamide)-ethyl)-benzenesulphonamide and 19.3 g of finely pulverized anhydrous potassium carbonate are suspended in 1000 ml of anhydrous dioxane. The mixture is heated to 80°C. and subsequently 30.4 g of ethyl chloroformate are added dropwise. The temperature is maintained for 12 hours and, after this time has elapsed, a solution of 13.1 g of cyclopentylamine and 10 g. of acetic acid in 10 ml of dioxane are added. The reaction mixture is heated under reflux for 2 hours, after which the dioxane is evaporated under reduced pressure, the residue is dissolved in a solution of 1 percent ammonium hydroxide and there is separated by filtration the insoluble fraction constituted by a small quantity of 4-(beta-(o-anisamide)-ethyl)-benzenesulphonamide which has not been converted to the desired product.

The ammonia solution is clarified with activated carbon and concentrated hydrochloric acid is added thereto up to substantially acid pH, whereupon the crude N-[4-beta-(o-anisamide)-ethyl)-benzenesulphonyl]-N'-cyclopentylcarbamide precipitates. The product is recrystallized in absolute ethanol. The melting point is 173° – 175°C.

The water soluble sodium or potassium salt may be formed with the corresponding alkali.

EXAMPLE 2

A diabetic patient having high level of blood sugar but who does have functionally active pancreatic beta cells is administered the N-[4-beta-(o-anisamide-ethyl)-benzenesulphonyl]-N'-cyclopentylcarbamide in amounts up to 30 mg per day in the form of tablets each containing 10 mg of the compound. The lowering of blood sugar level is observed.

What is claimed is:

1. N-[4-beta-(o-anisamide-ethyl)-benzenesulphonyl]-N'-cyclopentylcarbamide or a salt thereof of a pharmaceutically acceptable acid.

2. Compound according to claim 1 wherein said compound is the free N-[4-beta-(o-anisamide-ethyl)-benzenesulphonyl]-N'-cyclopentylcarbamide.

* * * * *